United States Patent [19]
Bashyam

[11] Patent Number: 5,343,750
[45] Date of Patent: Sep. 6, 1994

[54] MANUAL ULTRASONIC SCANNER FOR COMPLEX SURFACES

[75] Inventor: Manohar Bashyam, Mason, Ohio

[73] Assignee: General Electric Company, Cincinnati, Ohio

[21] Appl. No.: 797,020

[22] Filed: Nov. 25, 1991

[51] Int. Cl.⁵ .............................................. G01N 29/26
[52] U.S. Cl. ........................................ 73/635; 73/629
[58] Field of Search ................ 73/620, 629, 633, 635, 73/637, 638, 639, 640, 642

[56] References Cited

U.S. PATENT DOCUMENTS

| | | | |
|---|---|---|---|
| 3,958,451 | 5/1976 | Richardson | 73/644 |
| 4,030,344 | 6/1977 | Northeved et al. | 73/67.8 |
| 4,096,755 | 6/1978 | Hause et al. | 73/598 |
| 4,212,207 | 7/1980 | Conradi | 73/623 |
| 4,361,044 | 11/1982 | Kupperman et al. | 73/623 |
| 4,474,064 | 10/1984 | Naruse et al. | 73/640 |
| 4,541,434 | 9/1985 | Okado | 128/660 |
| 4,625,557 | 12/1986 | Rutherford | 73/635 |
| 4,655,085 | 4/1987 | Tomizawa et al. | 73/638 |
| 4,807,476 | 2/1989 | Cook et al. | 73/633 |
| 4,862,748 | 9/1989 | Woodmansee | 73/641 |

Primary Examiner—John E. Chapman
Attorney, Agent, or Firm—Jerome C. Squillaro; Charles L. Moore, Jr.

[57] ABSTRACT

A light weight hand held ultrasonic scanner for ultrasonic flaw detection systems utilizes an omnidirectional rolling ball element which drive optical encoders for X-Y coordinate position location of flaws. The rolling ball element is mounted in a body for rolling contact with a surface to be inspected. An ultrasonic transducer is mounted at one end of a second hollow body attached to the first body. An ultrasound reflector is provided in the hollow body to reflect an ultrasound beam transversely out of the second body.

5 Claims, 2 Drawing Sheets

MANUAL ULTRASONIC SCANNER FOR COMPLEX SURFACES

BACKGROUND OF THE INVENTION

This invention relates to a manual ultrasound defect detection scanner and more particularly to a mouse based X-Y hand scanner for ultrasonic sound wave defect detection systems for complex surfaces.

Ultrasonic sound wave defect detection has found widespread application for defect detection in composite materials such as ceramics and reinforced synthetic resin materials such as epoxy and carbon filament structures. Ultrasonic defect detection may utilize pulse echo or through transmission ultrasound. In either event a flaw within the material reflects all or part of the passing ultrasound wave. By electronic processing of these reflections, such flaws as cracks, inclusions and delaminations are detected and located. For effective penetration of an ultrasound wave into the material being tested and for optimum processing of reflections, the sound waves should enter the material perpendicularly to its surface. With respect to flat panels and other planar shapes, perpendicularity of the sound wave is readily achieved. With other surfaces of more complex configurations, perpendicularity may be limited by the scanning apparatus in which the transducer element is attached, particularly if attached in a manner which prohibits or prevents unrestricted directional travel. For example, some scanners involve a relatively inflexible frame or grid with a transducer mounted on an arm or leg of the grid. Such a grid is passed over a surface to be inspected so that the transducer may perform its function. However, the grid structure prevents the transducer from making close contact with some regions of complex surfaces as well as preventing or inhibiting the described perpendicularity of the sound beam entering the surface under inspection.

OBJECTS OF THE INVENTION

It is an object of this invention to provide an improved manual transducer scanner device for ultrasonic defect detection systems.

It is another object of this invention to provide an improved hand held scanner device for ultrasonic defect detection systems.

It is a further object of this invention to provide an improved mouse based X-Y hand held scanner for ultrasonic defect detection systems.

SUMMARY OF THE INVENTION

A small hand held scanner similar to a computer pointing mouse includes therein a rolling ball adapted to roll over a surface to be inspected for defect detection and serve as a location component of the scanner and detected flaw.

This invention will be better understood when taken in connection with the following drawings and description.

DESCRIPTION OF A PREFERRED EMBODIMENT

Figure 1:
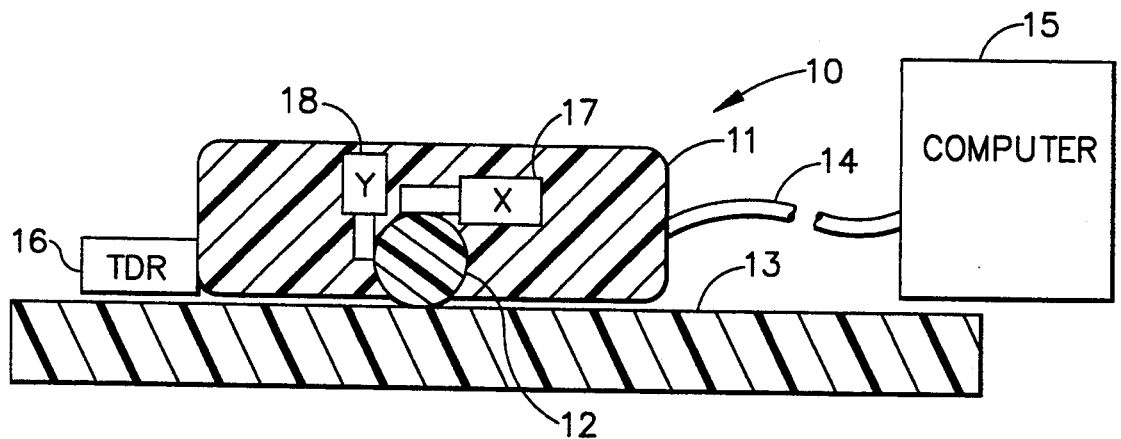
FIG. 1 is a schematic and cross-sectional view of the hand held scanner of this invention.

Referring now to FIG. 1, scanner 10 of this invention comprises a rectangular light weight body 11 incorporating therein rolling drive means in the form of a ball element 12 of a hard material of, for example, a synthetic resin or rubber material. Ball element 12 is located at a mid-point in body 11 and adapted to be freely rotatable omnidirectionally.

As illustrated in FIG. 1, sphere or ball element 12 projects a small distance from body 11 to not only roll on a surface 13 to be inspected, but also to space body 11 from surface 13. An electrical cable lead 14 connects scanner 10 to a computer and an electronic processor apparatus 15 which includes an electronic system and its components for appropriately processing electrical signals for ultrasonic flaw detection systems. One example of such a system and its components is disclosed in U.S. Pat. 4,807,476—Cook et al issued Feb. 2, 1989. An ultrasonic transducer 16 is affixed to one end of body 11 to be closely adjacent surface 13. Scanner 10 is adapted to be freely and easily manually traversed over the surface of a material to be inspected for subsurface flaws, and, because it is not attached to a rigid grid, it is free to follow curves and contours of a complex surface being inspected or evaluated. At the same time an ultrasound wave from transducer 16 is projected into the surface to be inspected with reflections from internal flaws being sensed and electronically processed in the usual manner for a visual representation of the flaw on a TV monitor or CRT. In order to establish coordinates of the position of a detected flaw in the underlying material, a pair of optical encoders 17 and 18 (X+Y coordinates) are positioned in body 11 to be associated with the rolling motion of ball element 12 as more clearly illustrated in FIG. 2.

Figure 2:
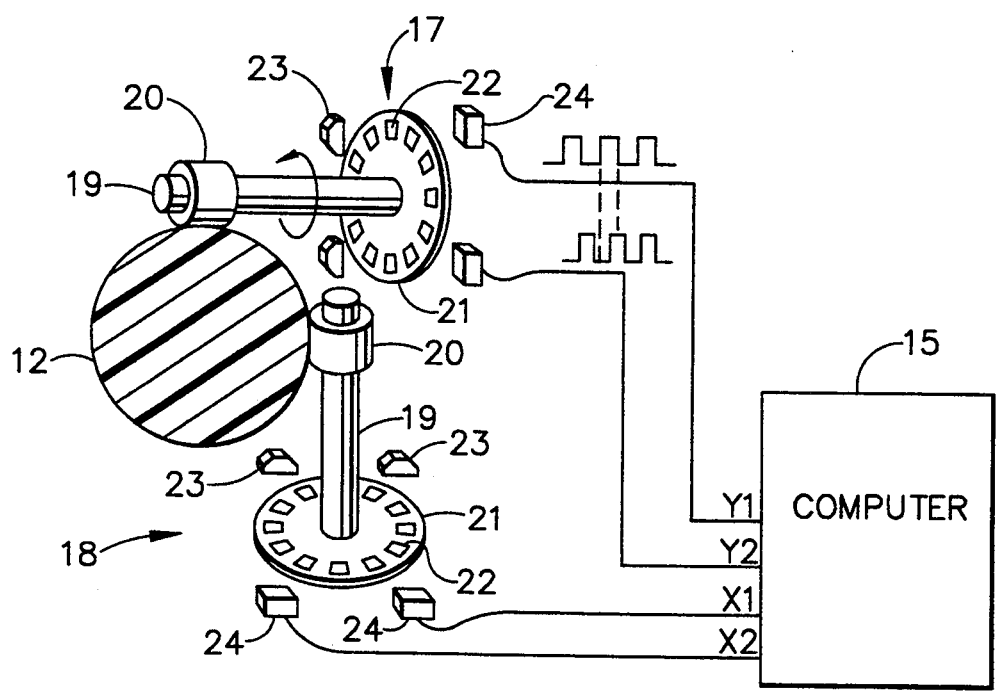
FIG. 2 is a schematic illustration of the internal mechanism and electrical circuitry in the scanner of this invention.

Referring now to FIG. 2, ball element 12 is mounted in body 11 (FIG. 1) for free and omnidirectional rotation. Ball element 12 is arranged to drive a pair of optical encoder means 17 and 18 (X+Y coordinates). Each encoder means 17 and 18 is identical to the other and with identical numerals such that a description of one suffices. In FIG. 2, encoder means 17 comprises a vertical shaft 19 with a friction drive means such as friction sleeve 20 at one end which is in contact with ball element 12 so that rotation of ball element 12 causes shaft 19 to rotate therewith. At the other end of shaft 19, a strobe-like disc 21 is concentrically fitted thereon for rotation by shaft 19. Strobe disc 21 is a light impervious disc with a peripheral row of spaced apertures 22 therethrough. An opposed pair of light projecting lamp means 23 and light detection means 24 are positioned on each side of disc 21 in coaxial alignment with each other through the row of apertures 22. A second encoder set of a shaft 19, strobe disc 21, and light projection and detection means 23 and 24 is positioned in vertical relationship to the first described set, as encoder 18.

In operation of encoder unit 17, for example, rolling motion of ball element 12 causes its shaft 19 to rotate and rotate strobe disc 21 between light projection means 23 and light detection means 24. Light detection means 24 is energized when an aperture of disc 20 is coaxially aligned with the axis of the light projection and detection means 23 and 24. Light then passes through disc 20 and is detected by detection means 24 which provides an electric signal to a transceiver and computer in processing system 15 as an X coordinate position, together with a Y coordinate from encoder 18. Each of the encoders 17 and 18 share a common rolling element drive means in the form of ball element 12. However, each encoder may have its own rolling drive means such as a wheel, roller, or disc which also engage the surface to be inspected. Each encoder provides its own X or Y signal to appropriate electronic circuitry and components in system 15 for processing as a scanner position signal which is then passed into a process computer in system 15. Reflected signals from ultrasonic transducer 16 as well as those from encoders 17 and 18 are stored in a computer to create a visual display as a C-scan image of a flaw and its position.

The invention as described is particularly adaptable for inspection of small radii curved surfaces as found, for example, at the innermost region of 90° flange structures. One example of this application is illustrated in FIG. 3.

Figure 3:
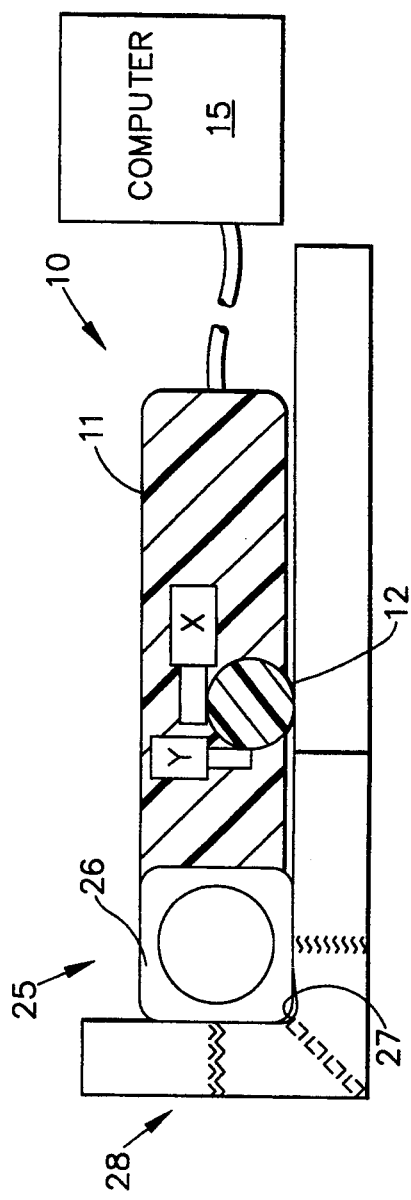
FIG. 3 is a schematic and cross-sectional view of one ultrasonic transducer assembly incorporated in the scanner of this invention.

Referring now to FIG. 3, scanner 10 of this invention includes a transducer assembly 25 which is attached to one smaller end of a rectangular body 11 similar to body 11 of FIG. 1. Rectangular body 11 includes the same internal components as described with respect to FIGS. 1 and 2, i.e. ball or sphere element 12, encoders 17 and 18 and related circuitry. Transducer assembly 25 comprises an elongated generally rectangular hollow body 26 having one longitudinal edge 27 rounded or formed to fit accurately and coincidentally into the innermost small radii curved surface of any general 90° angled member 28 such as a flange inner fillet which is to be inspected. Coincidence between the engaging surfaces eliminates larger areas without good ultrasound contact which would deleteriously affect the accuracy of detection, Body 26 also fits closely into the 90° flange angle 28 to have a full 90° contact with planar surface to planar surface contact along each leg of the 90° angle member 28, i.e. as opposed to a round probe which would not have planar surface contact in the flange angle. Further details of transducer assembly 26 are best described with respect to FIG. 4.

Figure 4:
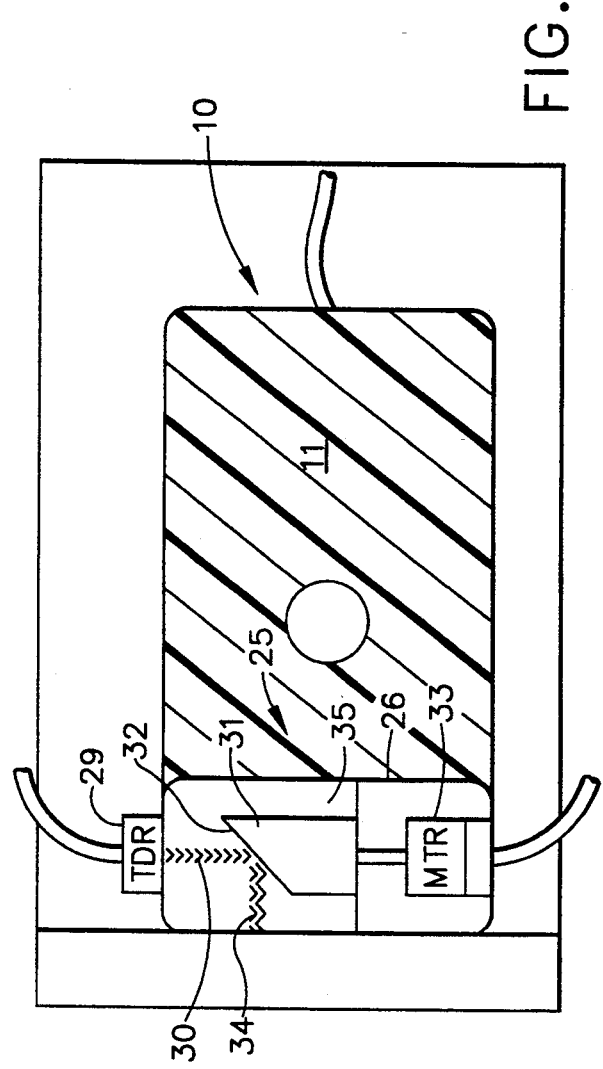
FIG. 4 is a cross-sectional and side view of the scanner of FIG. 3 in its operative angle inspecting position.

Referring now to FIG. 4, transducer assembly 25 comprises an ultrasonic transducer 29 at one end surface of rectangular body 26 and adapted to pass an ultrasonic signal 30 axially into body 26. Within body 26 a wedge reflector 31 is positioned to intercept sound wave 31 from ultrasonic transducer 29. Wedge reflector 31 includes a mirror surface 32 thereon accurately positioned at a 45° angle to sound wave beam 30. Wedge reflector 31 is conveniently produced from a stainless steel material with its 45° mirror surface 32 being a highly polished integral surface of wedge reflector 31. Also, wedge reflector 31 is adapted to be rotated about its longitudinal axis by an electric motor 33 positioned in body 26 at its end opposite transducer 29. In operation, rotating mirror 32 reflects ultrasound beam 30 at an angle of 90° to project transversely out of body 26 as beam 34. Rotation of mirror 32 also generates a 360° rotation of beam 34 as an ultrasound arc projecting into the small radii surface in flange member 28 in a perpendicular manner along its inner curved surface for a full 90° inspection. Body 26 includes a hollow chamber 35 in which wedge reflector 31 is positioned, and chamber 35 is filled with a fluid such as water or other highly sound conductive fluid medium for enhancement of reflected beam 34 from mirror 32. Ultrasound reflections from a detected flaw are sensed by transducer 29 and electronically processed and stored in a computer in system 15 (FIG. 1) to be presented visually on a CRT as a C scan image.

This invention provides a highly portable hand held ultrasound scanner utilizing a rolling ball element for traversing a surface to be inspected while at the same time utilizing the ball element as a mechanical drive means to drive a pair of separate encoders to establish the X-Y position of the scanner on the surface to be inspected. The scanner device is not limited to "desktop" systems where the part to be inspected must be transported to a desk or bench, but may be easily transported to the surface to be inspected. This is particularly advantageous where the scanner may be used to inspect surfaces which are preassembled into a component, to the extent that the component may have been assembled, for example, to an aircraft engine in an aircraft, and perhaps in a remote location.

The scanning mechanism as described is not only effective for use with an ultrasound system, but also may be gainfully employed with other non-destructive scanning systems such as an electrical current system, for example, an eddy current system.

While this invention has been described with respect to a preferred embodiment, it will be understood by those skilled in the art that various changes and modifications may be made without departing from the spirit and scope of the invention in the following claims.

What is claimed:

1. A hand held ultrasonic scanning device for manually traversing a surface of a material to be inspected for subsurface flaws, comprising:
   a first body;
   a second hollow body mounted on said first body;
   an ultrasonic transducer mounted at one end of Said second hollow body to generate and project an ultrasound beam axially into said second hollow body;
   an ultrasound reflector in said second hollow body and axially spaced from said transducer, said reflector being positioned at a 45° angle with respect to said transducer to reflect the ultrasound beam therefrom at a 90° angle transversely out of said second hollow body;
   drive means coupled to said reflector for rotating said reflector to cause said ultrasound beam to rotate through an arcuate path in a plane perpendicular to the surface to be inspected;
   an omnidirectional rolling element in said first body for rolling contact with the surface to be inspected; and
   a pair of encoders in said first body and operated by said omnidirectional rolling element to provide separate electrical signals representing position coordinates of said second hollow body on the surface.

2. The invention as recited in claim 1 wherein said omnidirectional rolling element comprises a hard material sphere mounted for omnidirectional rotation within said body and projecting therefrom to engage said surface.

3. The invention as recited in claim 1 wherein said body has one longitudinal edge formed as a matching and coincident curve to a flange angle fillet to be inspected.

4. The invention as recited in claim 1 wherein said reflector is submerged in a sound conductive fluid medium.

5. The invention as recited in claim 1 wherein said drive means comprises an electronic motor in said second hollow body.

* * * * *